Feb. 23, 1932.
R. L. CATRON
Plant Pat. 9
HYBRID TEA ROSE
Filed Dec. 13, 1930
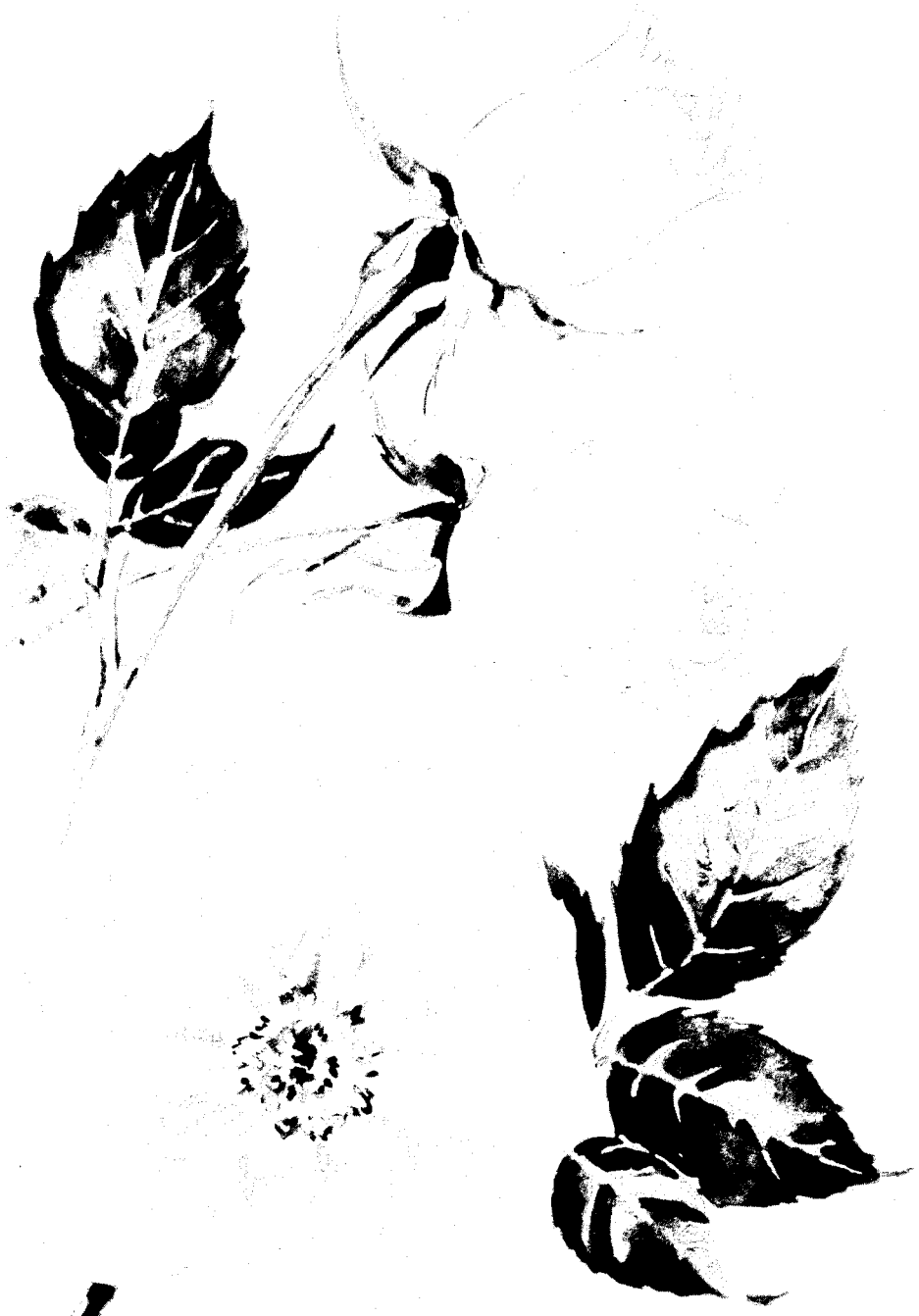
Inventor
Robert L. Catron
By Orville M. Kile agent:

Patented Feb. 23, 1932

UNITED STATES PATENT OFFICE

ROBERT LEE CATRON, OF RICHMOND, INDIANA, ASSIGNOR TO JOSEPH H. HILL COMPANY, OF RICHMOND, INDIANA, A CORPORATION

HYBRID TEA ROSE

Application filed December 13, 1930. Serial No. 502,219.

My invention relates to improvements in fragrant, yellowish-pink, double, hybrid tea roses. The object of my improvements is to provide a rose of the type mentioned having a distinctive orange-pink color in the bud assuming yellowish shades on portions of the petals as the flower opens; of good lasting qualities; stem relatively free from spines; free blooming; glossy green foliage; of vigorous growth; disease resistant, and having other desirable qualities.

This new rose is the result of definite breeding efforts carried on by myself and associates and originated through the crossing of an unnamed seedling with the pollen parent Sov. de Claudius Pernet. The improved seedling was first discovered by myself during or about the year 1929 and has since been propagated and developed. It is registered at the office of the American Rose Society.

The accompanying illustrations show in full color and in approximately natural size, a bud, a half opened flower and a fully opened flower.

The following is a detailed description of this rose.

A bush or upright rose of medium height, (5 to 6 feet) compact, vigorous of growth, a free bloomer, and resistant to disease.

Stem, stoutish, green, sparingly to moderately beset with stoutish retrorsely directed spines or prickles approximately straight or slightly convex on upper surface. The upper stem or peduncle is straightish to moderately sinuous or somewhat zigzagged.

Leaves on flower-bearing stems, 4 to 6 inches long, the blades glabrous; the petioles bearing scattered, glandular hairs as well as occasional short prickles. Leaflets, (3 to 5 and occasionally 6 or 7 on the second to fifth leaves) elliptical-ovate to ovate; apex abruptly and often symmetrically short-acuminate; margins non-uniformly sub-revolute, irregularly crenate-serrate; teeth often produced into slender points; blades deep, rich green above, with mid-rib and primary vein depressed; pale below. The color of the upper surface and the wavy marginal outline of the leaflets, due to the non-uniform revolute character of the margin, give a strong holly-like resemblance.

Stipules, sub-foliaceous; ¾ to 1 inch long including the slender, acuminate points; $\frac{3}{16}$ to $\frac{5}{16}$ inches wide, terminating in slender, subulate, bristle-like, ascending or spreading points, about $\frac{3}{16}$ inch in length; the margins densely set with glanular hairs.

Sepals, normally five, narrowly lanceolate, the basal portion about 1 inch long, produced into a long acuminate tip or occasionally into a subfoliaceous organ the length of the entire structure being ½ to 2 inches; inner surface of basal portion densely tomentose, the margins more or less closely beset with glandular hairs and occasionally bearing one or more linear-lanceolate foliaceous bracts near the base.

Buds, long, ovate-lanceolate; opening bud 1½ to 1¾ inches long.

Hips, short, stout, tapering rather abruptly to the peduncle.

Flower, double, borne singly on stems, 4 to 4¼ inches across when open.

Petals varying greatly from outer to inner whorls. Outer petals broadly obovate to sub-orbiculate, often abruptly apiculate, becoming more and more oblanceolate in successive whorls toward the center of the flower. Those of the innermost whorls often irregular in outline and finally greatly reduced and staminoid in character. Petals approximately 33 to 47 in number with average probably 40 to 42.

Color, effect in bud is from orange-pink gradually assuming yellowish to apricot yellow shades in the opening flower and fading out to lighter tints as the flower grows older, at any given time the yellow being deeper on the inner surface of the petal as compared with the outer surface and at the base of the petal as compared with the apex, the yellowish tints suffusing but not masking the pink as the petals age.

I claim:

The hybrid tea rose herein shown and described, chiefly characterized by its yellowish-pink color, glossy green foliage, relative freedom from spines on the stem, long foliaceous sepals, and its free blooming, vigorous growing and disease resistant qualities.

ROBERT LEE CATRON.